United States Patent [19]
Wolfbeis

[11] Patent Number: 5,108,932
[45] Date of Patent: Apr. 28, 1992

[54] PROCESS FOR THE QUANTITATIVE DETERMINATION OF AT LEAST ONE PARAMETER OF A LIQUID OR GASEOUS SAMPLE

[75] Inventor: Otto S. Wolfbeis, Graz, Austria

[73] Assignee: AVL AG, Schaffhausen, Switzerland

[21] Appl. No.: 386,996

[22] Filed: Jul. 31, 1989

[30] Foreign Application Priority Data

Aug. 2, 1988 [AT] Austria ................................. 1952/88

[51] Int. Cl.⁵ ............................................. G01N 21/64
[52] U.S. Cl. ..................................... 436/124; 356/317; 356/318; 356/417; 250/458.1; 250/459.1; 436/171; 436/172; 436/133; 436/136; 436/138; 436/163
[58] Field of Search ............... 436/124, 136, 172, 163, 436/133, 178, 171, 125, 138; 422/82.07, 82.06, 82.09, 82.11, 82.12, 82.13; 356/317, 318, 417; 128/634-636; 250/458.1-461.2

[56] References Cited

U.S. PATENT DOCUMENTS

| 4,548,907 | 10/1985 | Seitz et al. | 436/133 |
| 4,768,886 | 9/1988 | Hirschfeld et al. | 73/714 |
| 4,842,783 | 6/1989 | Blaylock | 350/96.29 |

FOREIGN PATENT DOCUMENTS 0336985 10/1989 European Pat. Off. .
2132348 2/1984 United Kingdom .
WO00023 1/1987 World Int. Prop. O. .

OTHER PUBLICATIONS

Gehrich, J. L.; Lübbers, D. W.; Hansmann, D. R; Miller, J. K.; Yafuso, M., "Optical Fluorescence and Its Application to an Intravascular Blood Gas Monitoring System", IEEE Transactions on Biomedical Engineering, vol. BME-33 (2) Feb. 1986, pp. 117-131.

Primary Examiner—Robert J. Hill, Jr.
Assistant Examiner—Thomas E. Daley
Attorney, Agent, or Firm—Watson, Cole, Grindle & Watson

[57] ABSTRACT

For the simultaneous measurement of two parameters of a liquid or gaseous sample, in a fluorescence measuring device in which the influence of the aging processes of the indicator substance and the fluctuations in the light intensity of the excitation light source are to be avoided, it is proposed that the change in the first parameter to be measured is obtained from the change in the ratio of two intensity values, determined for different wavelengths of the excitation and emission spectrum of the indicator substance, and the change of a second parameter is obtained from the change in the decay time t of the fluorescence radiation of the same indicator substance from the group of aromatic hydrocarbons, the aromatic heterocycles and the metal organic complexes.

18 Claims, 1 Drawing Sheet

PROCESS FOR THE QUANTITATIVE DETERMINATION OF AT LEAST ONE PARAMETER OF A LIQUID OR GASEOUS SAMPLE

BACKGROUND OF THE INVENTION

1. Technical Field of the Invention

The invention relates to a process for the quantitative determination of at least one parameter of a liquid or gaseous sample, in which process the fluorescence radiation of an indicator substance in direct or diffusion contact with the sample is measured, said fluorescence radiation being emitted following fluorescence excitation.

2. Discussion of the Related Art

In known measuring devices with optically active indicator substances or fluorescent dyes, the change in the excitation or emission spectrum that occurs with a change in the parameters to be measured or in the concentration of the substance to be determined is recorded, in which process the desired parameters or concentrations of the substance can be determined by means of suitable calibrating processes and calibrating substances. The terms "excitation spectrum" and "emission spectrum" shall be defined here and in the following manner, to obtain the excitation spectrum the wavelength of the excitation radiation is varied over its spectrum and the intensity of the emission radiation is measured at a specific wavelength. To obtain the emission spectrum the wavelength of the excitation radiation is held constant and the spectral intensity distribution of the emission radiation is measured. The excitation radiation is monochromatized in the conventional manner by means of suitable devices such as selective filters or prisms with subsequent slit diaphragm or with the aid of electronically tunable excitation light sources. The emission radiation is recorded, also as a function of the wavelengths, by means of a suitable measuring device.

Thus, for example, a measuring device, which has an indicator chamber that on the sample side is covered with a selectively permeable membrane and in which there is an organic indicator substance, is known from the DE-OS 2 508 637. In this known system specific organic compounds such as β-methyl umbelliferon are used as indicators that react with a change in their excitation spectrum in the solution containing the indicator, independent of the concentration of positive hydrogen ions. Thus in enabling the selective diffusion of hydrogen ions from the sample to be measured into the indicator chamber or the indicator solution, the hydrogen ion concentration or the pH value of the sample can also be measured.

It is also known from this document that the intensity of the emission spectrum of specific organic compounds such as the pyrene butyric acid is reduced by means of the presence of molecular oxygen on a scale that is largely comparable to the partial pressure of oxygen in the phase containing the indicator, with which such a device can also be used to measure the partial pressure of oxygen.

However, this known system has the drawback that the simultaneous measurement of the concentration of several different substances in the sample is relatively expensive. In addition to this, several indicator chambers lying next to one another are mandatory, each of which must contain an indicator substance that responds to the substance to be measured and which is excited via the respectively assigned monochromators and whose fluorescence radiation is evaluated by means of the corresponding suitable measuring devices.

Furthermore, it is known from AT-PS 377 364 that a substituted aromatic or heteroaromatic compound can be used as the organic indicator substance, in which process the substituted aromatic or heteroaromatic compound contains one or more substituents. Such indicators or indicator substances, which react in a clearly distinguishable manner to the change in the concentration of at least two different substances in the sample by a shade change in the excitation spectrum and intensity change in the emission spectrum, the change in the shade and the change in the intensity serving as a measure for the change in concentration of the substances to be detected, have as functional groups, in particular, at least one phenol, carboxylic acid, or sulfonic acid group, etc. or a combination of these groups. Thus organic indicator substances are used here that react to the change in the concentration of the substances to be measured in the sample by a shade alteration or intensity change in the fluorescence radiation emitted following excitation.

For example, an indicator substance can be used that reacts with a shade alteration of its excitation spectrum when the concentration of hydrogen ions in the sample changes and with an intensity change in its emission spectrum when the concentration of molecular oxygen in the sample changes, whereby the isosbestic wavelength remains at least approximately constant. When excited with the isosbestic wavelength, the intensity of the fluorescent light is by definition a pH independent variable and represents a measure for the entire concentration of the indicator substance contained in the indicator chamber.

There are certain drawbacks with this method since at least one sought parameter (here $O_2$) is a function exclusively of an intensity change in the fluorescence radiation and thus is a function of the aging processes (photo bleaching) of the indicator substance. In addition to this, fluctuations in the intensity of the excitation light source and the varying response sensitivity of the measuring device detecting the fluorescence radiation influence this measured value.

Since the definitive separation of the weakening and the shade alteration of the fluorescence radiation and the respective assignment to a change in the hydrogen ion concentration or change in the concentration of molecular oxygen in the sample is possible only if the isosbestic wavelength remains at least approximately constant at different $O_2$ concentrations, a selection criterion is assumed that is fulfilled only by few indicator substances.

The object of the present invention is to avoid the drawbacks of the indicator substances used for the aforementioned devices and/or processes and, thus, to improve in a simple manner the simultaneous measurement of two parameters of a sample, in which process the measured values shall not be influenced by the aging processes of the indicator substance, fluctuations in the light intensity of the excitation light source, and different detector efficiency.

SUMMARY OF THE INVENTION

These problems are solved in accordance with the present invention in that the change in the first parameter to be measured is obtained from the change in the ratio of two intensity values, determined for different wavelengths of the excitation and emission spectrum of the indicator substance, and the change of a second parameter is obtained from the change in the decay time t of the fluorescence radiation of the same indicator substance from the group of aromatic hydrocarbons, the aromatic heterocycles and the metal organic complexes.

Preferably not only the measurement of the decay time of the fluorescence radiation but also the change in the ratio of two intensity values of the excitation or emission spectrum is independent of the aging processes of the indicator substance and of the aforementioned disadvantageous effects of the measuring device so that two parameters of the sample can be determined in a simple manner with one indicator substance.

Thus it can be provided in accordance with the invention that a sulfonic acid anilide or a hydroxyl derivative of a polycyclic aromatic hydrocarbon or a heterocyclic compound is used as the indicator substance, wherein the pH value is acquired with the intensity ratio and the $O_2$ concentration of the sample is acquired with the decay time t of the fluorescence. For example, a phenol from the group of hydroxyanthracenes, hydroxynaphthalenes, and hydroxypyrenes can be used. An example of a field of application would be the blood gas analysis, where besides the $O_2$ content, the precise determination of the pH value of the blood is also always mandatory. Another field of application is in bioprocess technology, especially with the fermentor probes of bioreactors.

According to another feature of the invention, eosin or a 7-hydroxycoumarin can be used as another indicator substance, in which process the pH value is acquired with the intensity ratio and the temperature of the sample is acquired with the fluorescence decay time t. As an example of application reference can be made again to the blood gas analysis, where it is necessary to measure the temperature for a precise determination of the pH value. Thus expensive thermostatizations of the measuring device can be eliminated. In addition to this, the indicator substances listed here are largely independent of the $O_2$ content of the sample. Other advantageous applications are possible whenever measurements are to be made under non-thermostatized conditions. Since almost all sensors are temperature dependent, the method of the invention offers for the first time the possibility of being able to measure with a correction for the temperature without an additional temperature sensor element.

For blood gas analyses, $O_2$ concentration, temperature, and pH value can also be determined, for example, with two indicator layers of which one contains, for example, hydroxyanthracene and the other eosin, in which process the measured value for the pH is derived from each of the two indicator substances and one of the values can be used as the test value for all of the other values. In this manner measurements can be conducted rapidly and reliably.

Another embodiment of the invention provides that a solution of 1-hydroxypyrene-3,6,8-trisulfonate in a bicarbonate buffer is used as the indicator substance that is embedded in a silicone polymer, in which process the $CO_2$ concentration of the sample is acquired with the intensity ratio and the temperature of the sample is acquired with the fluorescence decay time t. The change in the pH value, produced by the $CO_2$, brings about a change in the fluorescence of the indicator. The partial pressure of $CO_2$ is determined from the ratios of two intensity values of the emission spectrum, measured at 520 nm at an excitation wavelength of 460 or 410 nm. At the same time the temperature is determined by measuring the fluorescence decay time at an excitation wavelength of 460 nm and by measuring the fluorescence at 520 nm.

The invention also provides that 7-hydroxy-N-methylquinolinium is used as the indicator substance, in which process the pH value is acquired with the intensity ratio and the chloride concentration of the sample is acquired with the change in the fluorescence decay time t.

The measurement process of the invention also provides that the indicator substance, in contact with the sample and having a known or previously determined fluorescence decay time $t_o$, is excited with modulated light, and the fluorescence decay time t is determined from the phase shift between excitation radiation and fluorescence radiation, that the value of the second parameter is determined from the ratio of $t : t_o$, and that the value of the first parameter is determined from the ratio of two intensity values of the emission spectrum, measured at different wavelengths. The change in decay time and thus, for example, the $O_2$ content of a sample is determined phase fluorimetrically; the change in pH value is determined by means of the intensity ratio.

In another embodiment of the invention it is also possible that the indicator substance, in contact with the sample and having a known or previously determined, unquenched fluorescence decay time $t_o$, is excited with a light pulse, that at least two intensity values are obtained within the decay period and from this the fluorescence decay time t is determined. Both methods, not only the phase fluorimetric but also the pulse method, have already been described in another context in the AT-PS (186/86) of the inventor. Here, however, only one substance can be determined with one indicator substance—for example, for the measurement of oxygen a metal organic complex of the elements ruthenium or iridium.

Finally, according to the invention it is also possible that the shift of the fluorescence maximum be detected to determine the change in the spectral intensity distribution of the fluorescence radiation.

The invention is explained in detail with reference to the drawings as follows.

DETAILED DESCRIPTION OF THE PREFERRED EMBODIMENTS

Figure 1:
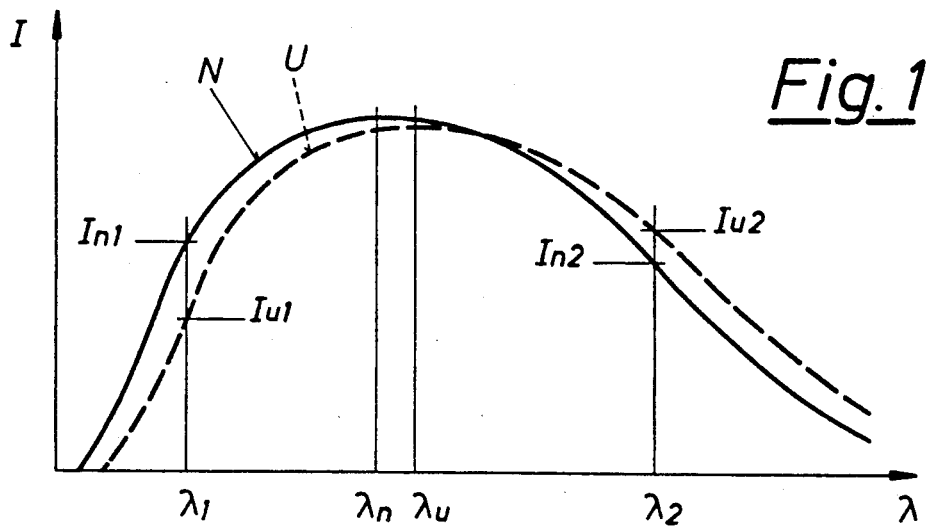
FIG. 1 shows the emission spectra of an indicator substance of the invention.

In the diagram, shown in FIG. 1, the intensity I of the fluorescence radiation is plotted on the ordinate and the wavelength lambda is plotted on the abscissa. The emission spectrum of an indicator substance of the invention, for example eosin, for a neutral solution with pH=7 is shown with the solid line N; the emission spectrum of the unknown sample whose pH value is to be determined is shown with the dashed line U. Following the determination of the intensity ratio $I_{u1}/I_{u2}$ of an unknown sample to be measured with the aid of a calibrating function, which produces a correlation between pH value and intensity ratio, the pH value of the unknown sample can be determined from the intensity ratio $I_{n1}/I_{n2}$, which is known or to be determined once, at the wavelengths $lambda_1$ or $lambda_2$ of a neutral sample. In the example shown, the unknown sample is basic.

Since the intensity ratio is independent of the aging processes of the indicator substance and independent of the fluctuations in the sensitivity of the detector or intensity of the excitation light, the pH value can be determined independently of these disturbance variables. Independent of the intensity measurements, the second parameter, the temperature, for example, is measured phase fluorimetrically.

Of course, it is also possible to determine the change in the pH value via the shift in maximum of the fluorescence radiation from $lambda_n$ to $lambda_u$.

Figure 2:
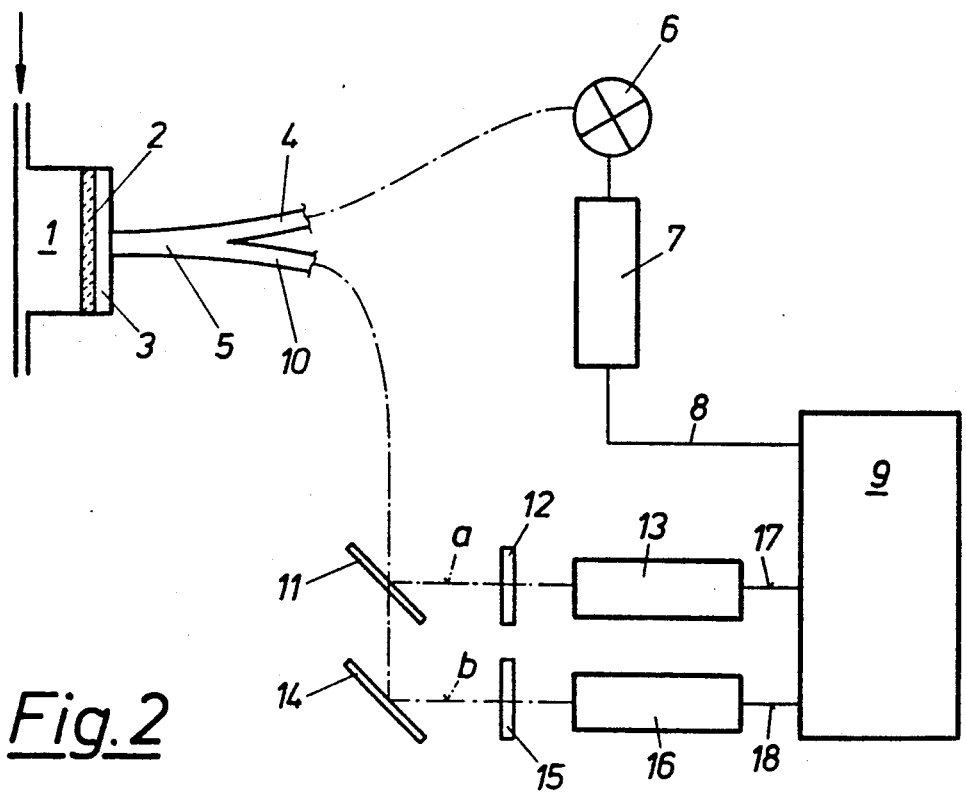
FIG. 2 is a schematic presentation of a corresponding measuring device.

Another possible embodiment of the measuring device of the invention is shown in FIG. 2. The liquid or gaseous sample in a measuring chamber 1 makes contact via a membrane 2 with the indicator substance 3, immobilized in a suitable manner in the measuring chamber, in which process the parameters to be determined change their fluorescence behavior. The indicator substance 3 is guided by means of an arm 4 of a two-armed light guide 5 with the aid of a light source 6 modulated excitation radiation, in which process the energy supply 7 of the light source 6 is connected to a control and evaluation unit 9 by means of a control line 8. The second arm 10 of the two-armed light guide 5 leads to a beam splitter 11, where the first partial beam a is guided to a unit comprising a filter 12 and a detector 13. The second partial beam b is guided via a mirror 14 to a second unit, comprising a filter 15 and detector 16. The two filters permit only radiation of wavelength $lambda_2$ or $lambda_2$ to pass. In the evaluation unit 9 connected to the detectors 13, 16 by means of the signal lines 17, 18, the ratios of the signal levels are formed by the two lines 17 and 18 and computed from a stored calibrating function of the pH value. The second variable to be determined is determined from the angle of the phase shift between the excitation radiation and one of the partial beams a or b.

Of course, it is also possible to use only one detector, which is connected in front of a chopper wheel with two filters of different permeability; thus mirror and beam splitter in the optical path are eliminated and errors stemming from different response functions of the two detectors can be avoided.

We claim:

1. Process for the quantitative determination of a first and a second parameter of a liquid or gaseous sample, comprising the steps of:
   measuring the fluorescence radiation of an indicator substance selected from the group consisting of aromatic hydrocarbons, aromatic heterocycles and metal organic complexes in direct or diffusion contact with the sample, said fluorescence radiation being emitted following fluorescence excitation;
   obtaining the change of said first parameter from the change in the ratio of two intensity values which are determined for different wavelengths of the excitation spectrum of the indicator substance; and
   obtaining the change of said second parameter from the change in the decay time of the fluorescence radiation of the same indicator substance.

2. Process, as claimed in claim 1, wherein a sulfonic acid anilide or a hydroxyl derivative of a polycyclic aromatic hydrocarbon or a heterocyclic compound is selected as the indicator substance, and wherein the first parameter is the pH value of the sample and the second parameter is the $O_2$ concentration of the sample.

3. Process, as claimed in claim 1, wherein eosin or a 7-hydroxycoumarin is selected as the indicator substance, and wherein the first parameter is the pH value of the sample and the second parameter is the temperature of the sample.

4. Process, as claimed in claim 1, wherein a solution of 1-hydroxypyrene-3,6,8-trisulfonate in a bicarbonate buffer is selected as the indicator substance and further comprising the step of embedding the indicator substance in a silicone polymer, and wherein the first parameter is the $CO_2$ concentration of the sample and the second parameter is the temperature of the sample.

5. Process, as claimed in claim 1, wherein 7-hydroxy-N-methyl-quinolinium is selected as the indicator substance, and wherein the first parameter is the pH value of the sample and the second parameter is the chloride concentration of the sample.

6. Process, as claimed in claim 1, wherein the indicator substance, in contact with the sample and having a known or previously determined fluorescence decay time $t_o$, is excited with modulated light, and the fluorescent decay time t is determined from the phase shift between excitation radiation and fluorescence radiation, wherein the value of the second parameter is determined from the ratio of $t:t_o$, and wherein the value of the first parameter is determined from the ratio of two intensity values of the emission spectrum, measured at different wavelengths.

7. Process, as claimed in claim 6, wherein the shift of the fluorescence maximum is acquired to determine the change in the spectral intensity distribution of the fluorescence radiation.

8. Process, as claimed in claim 1, wherein the indicator substance, in contact with the sample and having a known or previously determined, unquenched fluorescence decay time $t_o$, is excited with a light pulse, wherein at least two intensity values are obtained within the decay period and from this the fluorescence decay time t is determined.

9. Process, as claimed in claim 7, wherein the shift of the fluorescence maximum is acquired to determine the change in the spectral intensity distribution of the fluorescence radiation.

10. Process for the quantitative determination of a first and a second parameter of liquid or gaseous sample, comprising the steps of:
    measuring the fluorescence radiation of an indicator substance selected from the group consisting of aromatic hydrocarbons, aromatic heterocycles and metal organic complexes in direct or diffusion contact with the sample, said fluorescence radiation being emitted following fluorescence excitation;
    obtaining the change of said first parameter from the change in the ratio of two intensity values which are determined for different wavelengths of the emission spectrum of the indicator substance; and
    obtaining the change of said second parameter from the change in the decay time of the fluorescence radiation of the same indicator substance.

11. Process, as claimed in claim 10, wherein a sulfonic acid anilide or a hydroxyl derivative of a polycyclic aromatic hydrocarbon or a heterocyclic compound is selected as the indicator substance, and wherein the first parameter is the pH value of the sample and the second parameter is the $O_2$ concentration of the sample.

12. Process, as claimed in claim 10, wherein eosin or a 7-hydroxycoumarin is selected as the indicator substance, and wherein the first parameter is the pH value of the sample and the second parameter is the temperature of the sample.

13. Process, as claimed in claim 10, wherein a solution of 1-hydroxypyrene-3,6,8-trisulfonate in a bicarbonate buffer is selected as the indicator substance and further comprising the step of embedding the indicator substance in a silicone polymer, and wherein the first parameter is the $CO_2$ concentration of the sample and the second parameter is the temperature of the sample.

14. Process, as claimed in claim 10, wherein 7-hydroxy-N-methyl-quinolinium is selected as the indicator substance, and wherein the first parameter is the pH value of the sample and the second parameter is the chloride concentration of the sample.

15. Process, as claimed in claim 10, wherein the indicator substance, in contact with the sample and having a known or previously determined fluorescence decay time $t_o$, is excited with modulated light, and the fluorescence decay time t is determined from the phase shift between excitation radiation and fluorescence radiation, wherein the value of the second parameter is determined from the ratio of $t:t_o$, and wherein the value of the first parameter is determined from the ratio of two intensity values of the emission spectrum, measured at different wavelengths.

16. Process, as claimed in claim 15, wherein the shift of the fluorescence maximum is acquired to determine the change in the spectral intensity distribution of the fluorescence radiation.

17. Process, as claimed in claim 10, wherein the indicator substance, in contact with the sample and having a known or previously determined, unquenched fluorescence decay time $t_o$, is excited with a light pulse, wherein at least two intensity values are obtained within the decay period and from this the fluorescence decay time t is determined.

18. Process, as claimed in claim 16, wherein the shift of the fluorescence maximum is acquired to determine the change in the spectral intensity distribution of the fluorescence radiation.

* * * * *